(12) United States Patent
Ogawa

(10) Patent No.: US 8,912,507 B2
(45) Date of Patent: Dec. 16, 2014

(54) LIGHT IRRADIATION DEVICE FOR DENTAL IMPLANTS

(75) Inventor: Yoshimasa Ogawa, Okayama (JP)

(73) Assignee: Ushio Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 13/823,721

(22) PCT Filed: Sep. 5, 2011

(86) PCT No.: PCT/JP2011/070162
§ 371 (c)(1),
(2), (4) Date: Mar. 14, 2013

(87) PCT Pub. No.: WO2012/043156
PCT Pub. Date: Apr. 5, 2012

(65) Prior Publication Data
US 2013/0189642 A1    Jul. 25, 2013

(30) Foreign Application Priority Data
Sep. 30, 2010   (JP) .................................. 2010-221827

(51) Int. Cl.
*A61L 2/10* (2006.01)
*A61C 8/00* (2006.01)

(52) U.S. Cl.
CPC .............. *A61C 8/0089* (2013.01); *A61C 8/0022* (2013.01); *A61L 2/10* (2013.01)
USPC ........................................ 250/455.11; 422/24

(58) Field of Classification Search
USPC ........................................ 250/455.11; 422/24
See application file for complete search history.

(56) References Cited

U.S. PATENT DOCUMENTS

| 5,443,801 A | * | 8/1995 | Langford ...................... 422/294 |
| 5,547,635 A |   | 8/1996 | Duthie, Jr. |
| 5,688,475 A |   | 11/1997 | Duthie, Jr. |
| 6,402,517 B1 |  | 6/2002 | Hozumi et al. |

(Continued)

FOREIGN PATENT DOCUMENTS

| EP | 0 079 827 A1 * | 5/1983 |
| JP | S62-40730 A | 2/1987 |

(Continued)

OTHER PUBLICATIONS

Japan Patent Office, Office Action for Japanese patent application No. 2010-221827, Jul. 2, 2013.

(Continued)

*Primary Examiner* — Phillip A Johnston
*Assistant Examiner* — Hsien Tsai

(57) ABSTRACT

A light irradiation device for dental implants, which is capable of reliably performing a required ultraviolet ray irradiation treatment to screw type dental implants, is provided. The light irradiation device for dental implants irradiates screw type dental implants with ultraviolet rays wherein each of the screw type implants has a screw part comprising a spiral protrusion. The light irradiation device comprises a casing, a stage that is provided within the casing, in which the plurality of dental implants are disposed and held so as to be aligned in one direction, and an ultraviolet ray irradiation lamp that is disposed within the casing, wherein the entire surface of the protrusion that forms the screw part of each of the plurality of dental implants held on the stage is irradiated with the ultraviolet rays emitted from the ultraviolet ray irradiation lamp.

9 Claims, 4 Drawing Sheets

(56) References Cited

U.S. PATENT DOCUMENTS

| | | | |
|---|---|---|---|
| 2004/0118427 A1* | 6/2004 | Palfy et al. | 134/1 |
| 2005/0013729 A1* | 1/2005 | Brown-Skrobot et al. | 422/24 |
| 2007/0071789 A1* | 3/2007 | Pantelidis et al. | 424/423 |

FOREIGN PATENT DOCUMENTS

| | | | |
|---|---|---|---|
| JP | S62-040730 A | | 2/1987 |
| JP | H01-207070 A | | 8/1989 |
| JP | H04-264723 A | | 9/1992 |
| JP | 2000-66003 A | | 3/2000 |
| JP | 2000-066003 A | | 3/2000 |
| JP | 3072373 B1 | | 7/2000 |
| JP | 2001-017447 A | | 1/2001 |
| JP | 2001-269358 A | | 10/2001 |
| JP | 2005-080808 A | | 3/2005 |
| JP | 2005-80808 A | | 3/2005 |
| JP | 3144409 U | * | 8/2008 |
| JP | 2010-68875 A | | 4/2010 |
| JP | 2010-068875 A | | 4/2010 |

OTHER PUBLICATIONS

International Search Report for International Application No. PCT/JP21011/070162, Nov. 29, 2011.

Japan Patent Office, Office Action for Japanese Patent Application No. 2010-221827, Apr. 16, 2013.

* cited by examiner

LIGHT IRRADIATION DEVICE FOR DENTAL IMPLANTS

TECHNICAL FIELD

The present invention relates to a light irradiation device for dental implants, which irradiates, with ultraviolet rays, screw type dental implants, each of which has a screw part formed of a spiral protrusion.

BACKGROUND ART

A dental implant is implanted in a jawbone in order to substitute a function of a lost tooth therewith, and Patent Literature Document 1 discloses such a screw type dental implant in which a screw part formed of a spiral protrusion to be implanted in an alveolar bone, is formed. And, in a dental implant operation, it is important that the dental implant is fully combined with the bone (Osseointegration), so that in the Patent Literature Document 1, it is proposed that organic matters are removed by irradiating the dental implant with ultraviolet rays.

It is desired that in a light irradiation device, which irradiates such a dental implant with ultraviolet rays, the screw part which is implanted in the alveolar bone etc., be certainly irradiated with ultraviolet rays, and further two or more dental implants be simultaneously irradiated with ultraviolet rays since in one dental implant operation, the two or more dental implants are usually used. However, a light irradiation device, which suitably irradiates the two or more screw type dental implants with ultraviolet rays, was not known.

CITATION LIST

Patent Literature Document(s)

Patent Literature Document 1: Japanese Patent No. 3072373

Technical Problem

The present invention was made in view of the above background, and it is an object of the present invention to offer a light irradiation device for dental implants, which can certainly perform a necessary ultraviolet irradiation treatment to the screw type dental implants.

Solution to Problem

A light irradiation device for dental implants according to the present invention, which irradiates, with ultraviolet rays, screw type dental implants in each of which a screw part formed of a spiral protrusion, is formed, comprises a casing; a stage, which is provided in the casing and which is arranged and held so that the two or more dental implants may be aligned along one direction; and an ultraviolet ray irradiation lamp arranged in the casing, wherein the entire surface of the protrusion, which forms the screw part of each of the dental implants held on the stage, is irradiated with ultraviolet rays emitted from the ultraviolet ray irradiation lamp.

In the light irradiation device for dental implants according to the present invention, it is preferred that two ultraviolet ray irradiation lamps be arranged on both sides which are parallel to the one direction of an implant group made up of the dental implants held on the stage. Moreover, it is preferred that a reflecting mirror, which reflects the ultraviolet rays from the ultraviolet ray irradiation lamp, be arranged in the casing, and the entire surface of the protrusion, which forms a screw part of each of the dental implants, be irradiated with ultraviolet rays in form of direct light from the ultraviolet ray irradiation lamp and reflection light from the reflecting mirror. Moreover, it is preferred that a surface of the stage be formed as a light reflecting face.

Advantageous Effects of Invention

According to the light irradiation device for dental implants according to the present invention, since the entire surface of the protrusion which forms the screw part of each of the two or more dental implants arranged so as to be aligned along the one direction, is irradiated with the ultraviolet rays emitted from the ultraviolet ray irradiation lamp arranged in the treatment room, it is possible to certainly perform a desirable ultraviolet irradiation treatment to the screw type dental implants.

DESCRIPTION OF EMBODIMENT

Figure 1:
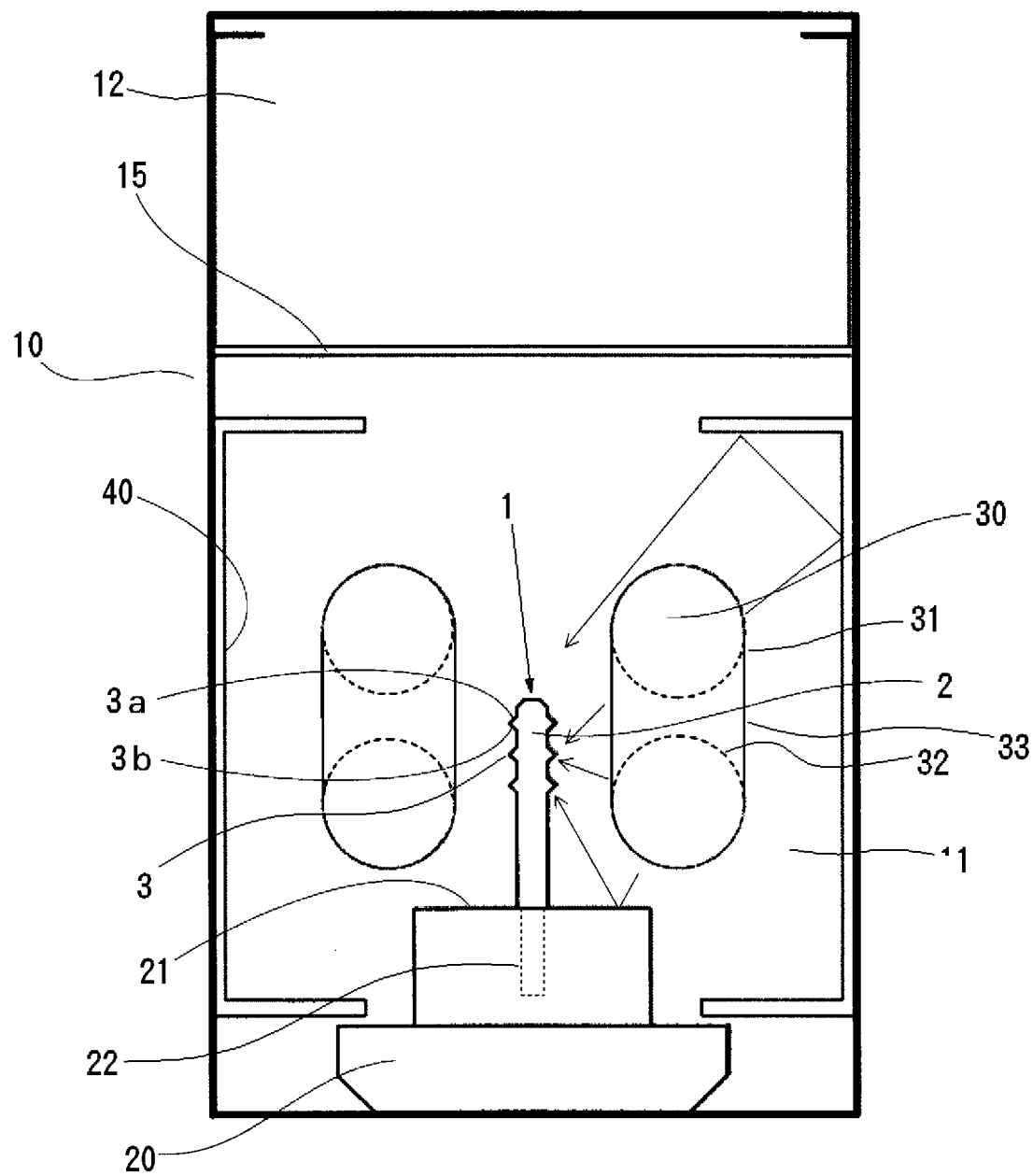
FIG. 1 It is an explanatory front view showing the structure of the inside of a casing in an example of a light irradiation device for dental implants according to the present invention.
Figure 2:
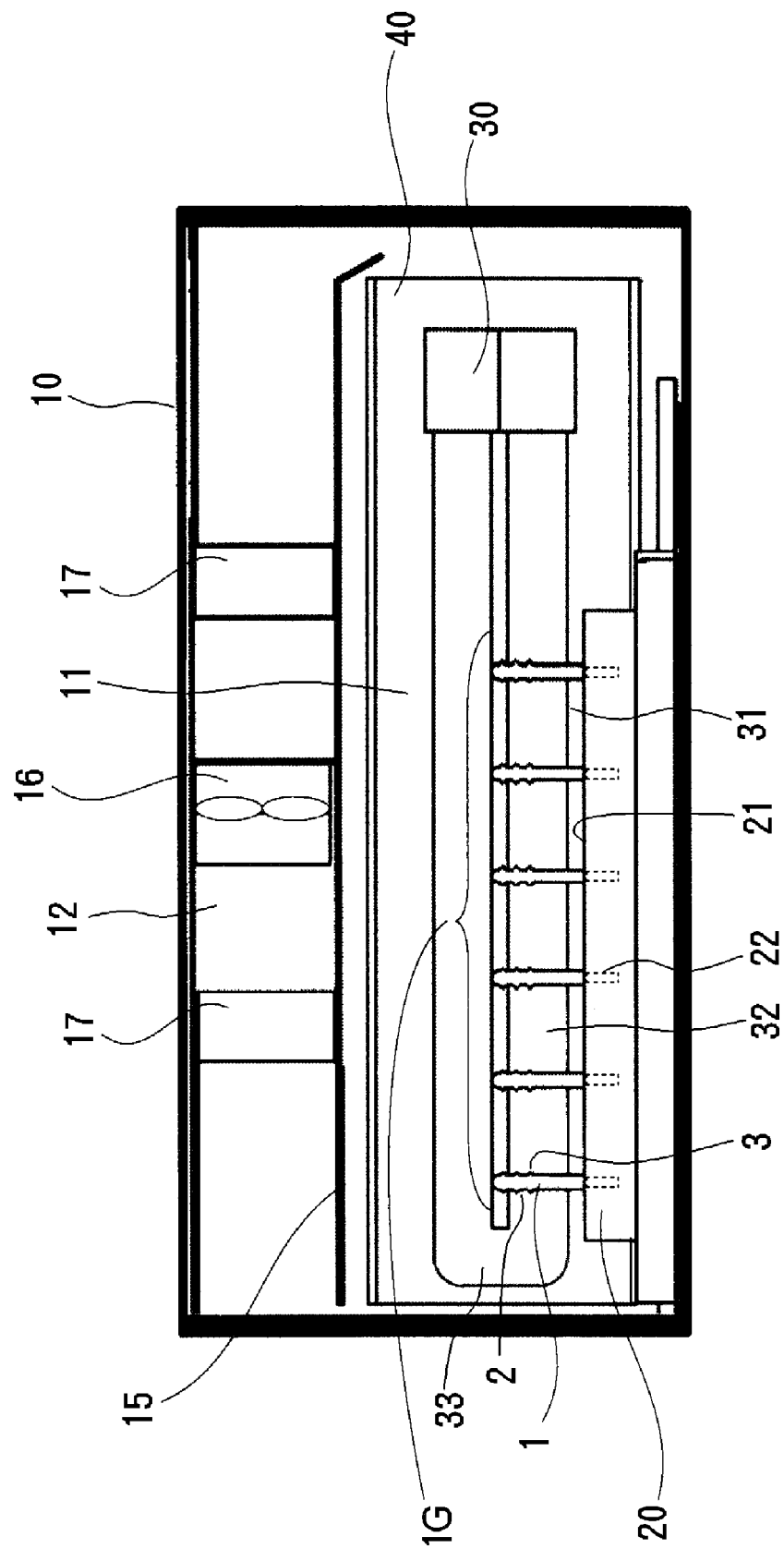
FIG. 2 It is a side view for explanation, showing the structure of the inside of a casing in an example of a light irradiation device for dental implants according to the present invention.

FIG. 1 is an explanatory front view showing the structure of the inside of a casing in an example of a light irradiation device for dental implants according to the present invention, and FIG. 2 is an explanatory side view showing the structure of the inside of the casing in the example of the light irradiation device for dental implants according to the present invention.

This light irradiation device for dental implants 1 (hereinafter merely referred to as a "light irradiation device") is used to irradiate pin-shaped dental implants (hereinafter also merely referred to as "implants") with ultraviolet rays, and has a casing 10 whose contour is a cuboid as a whole, wherein an opening and closing door (not shown in the figure) is provided at the front face thereof. While a treatment room 11, in which two or more implants 1 are placed, is formed inside this casing 10, an ozone removal room 12, which removes ozone produced in the treatment room 11, is formed above the treatment room 11, wherein the treatment room 11 and the ozone removal room 12 are separated from each other by a dividing wall 15. Each of the implants 1 arranged in the treatment room 11 of the casing 10 is of a screw type, which has a screw part 2, wherein the screw part 2 includes a protrusion 3, which is spirally formed at an end part thereof.

Inside the treatment room 11 of the casing 10, a stage 20 is provided so that the two or more implants 1 may be arranged and held thereon so as to be aligned along one direction (a direction perpendicular to a paper face on which FIG. 1 is drawn and horizontal directions in FIG. 2). Specifically, two or more holding portions 22, which consist of concave portions whose inner diameter matches the outer diameter of the other end parts of the respective implants 1, are formed so as to be aligned along the one direction on the surface 21 of the stage 20. The other end part of the implant 1 is inserted and held in each of these holding portions 22 in such an orientation that the implant 1 stands erect so that the tip of the screw part 2 of the implant 1 may be directed upward, whereby the two or more implants 1 are arranged so as to be aligned along the one direction, while each screw part 2 thereof is exposed in the treatment room 11. Thus, by arranging each of the implants 1 in an exposed state in the treatment room 11, it is possible to certainly irradiate, with ultraviolet rays emitted from the ultraviolet ray irradiation lamps 30, which will be described below, the entire surface of the protrusion 3 of the screw part 2 of each of the implants 1. Moreover, in an example shown in the figures, the surface of the stage 20 is, for example, mirror-finished, so that it may serve as a light reflecting face for reflecting the ultraviolet rays emitted from the ultraviolet ray irradiation lamp 30, which will be described below. Moreover, the stage 20 may be detachably attached to the casing 10. Since it becomes possible to take out the stage 20 to the outside of the casing 10 according to such structure, an attachment operation of the implants 1 to the stage 20, a detachment operation therefrom, or a replacement operation thereof can be easily performed.

The two ultraviolet ray irradiation lamps 30 are provided on both sides, which are parallel to the one direction, where the implants 1, which form an implant group 1G (which is made up of the two or more implants 1 held on this stage 20) are aligned. In particular, each of the ultraviolet ray irradiation lamps 30 has a U-shaped tube-like arc tube 31, in which two straight portions 32 extending in the one direction where the implants 1 are respectively aligned, are connected to each other by a curve portion 33. The two ultraviolet ray irradiation lamps 30 are arranged to face each other, through the screw parts 2 of the implants 1 and the spatial region of circumference thereof, in such an orientation that the two straight portions 32 of the arc tube 31 may be located on upper and lower sides thereof respectively. Moreover, two U-shaped gutter like reflecting mirrors 40, which reflect ultraviolet rays emitted from the ultraviolet ray irradiation lamps 30, are arranged between each of the ultraviolet ray irradiation lamps 30 and a side wall face of the treatment room 11, so as to face the respective ultraviolet ray irradiation lamps 30.

Low pressure mercury lamps, which emit ultraviolet rays whose wavelength is 254 nm and 185 nm, can be used as the ultraviolet ray irradiation lamps 30. Moreover, the illuminance of the ultraviolet rays emitted from the ultraviolet ray irradiation lamps 30 is, for example, approximately 6 mW/cm$^2$ or more at a position apart by 10 mm from the tube wall of the arc tube 31. The specification of an example of such low pressure mercury lamps used as the ultraviolet ray irradiation lamps 30 is given below. The arc tube is made from synthetic quarts glass, wavelength thereof is 200 mm and a lamp input is 25 W.

A fan 16, which circulates atmosphere gas in the treatment room 11 through the ozone removal room 12, is arranged in the ozone removal room 12 of the casing 10. Ozone removal filters 17 are arranged upstream and downstream of this fan 16, respectively.

In such a light irradiation device, the implants 1 are held in the respective holding portions 22 of the stage 20 in an orientation that the tips of the screw parts 2 may face upwards, and in this condition, each of the ultraviolet ray irradiation lamps 30 is turned on, whereby the protrusions 3, which form the respective screw parts 2 of the implants 1, are not only directly irradiated with the ultraviolet rays from the ultraviolet ray irradiation lamps 30 but also irradiated with those reflected by the reflecting mirror 40 and the surfaces of the stage 20. As a result, the entire surfaces of the protrusions 3 are irradiated with ultraviolet rays, and oxygen in the atmosphere gas in the treatment room 11 is irradiated with the ultraviolet rays from the ultraviolet ray irradiation lamps 30, whereby ozone is produced in the treatment room 11, so as to be in contact with the screw parts 2 of the implants 1. Thus, the entire surfaces of the protrusions 3 which form the respective screw parts 2 of the implants 1, that is, both an upper face 3a and a lower face 3b of each protrusion 3 are irradiated with the ultraviolet rays, and when ozone is in contact with the screw parts 2, organic matters adhering to the screw parts 2 of the implants 1 are decomposed and removed therefrom, whereby a washing treatment of the implants 1 is attained.

And after the washing treatment of the implants 1 is completed and the ultraviolet ray irradiation lamps 30 are turned off, the fan 16 is operated so that the atmosphere gas in the treatment room 11 is circulated through the ozone removal filter 17 arranged in the ozone removal room 12, whereby removal of the ozone in the treatment room 11 is performed, and after that, the implants 1 are taken out of the inside of the treatment room 11.

In the above example, the irradiation time of the ultraviolet rays emitted from the ultraviolet ray irradiation lamp 30 is, for example, 5 to 30 minutes. Moreover, it is preferred that the concentration of the ozone produced by irradiation of ultraviolet rays is 100 ppm or more, and preferably 200-400 ppm. Moreover, operation time of the fan 16, i.e., the ozone removal processing time is, for example, 10 to 300 seconds.

According to the light irradiation device, the two ultraviolet irradiance lamps 30 are arranged so as to face each other on both sides, which are parallel to the one direction of the implant group 1G made up of two or more implants 1 arranged so as to be aligned along the one direction, through the screw parts 2 of the implants 1 and the space region of the circumference thereof. Furthermore, since the two reflecting mirrors 40, each of which has a U-shaped gutter-like shape in cross section and which reflect ultraviolet rays from the ultraviolet irradiance lamp 30, are arranged so as to face the respective ultraviolet irradiance lamp 30, the protrusion 3, which forms the screw part 2 of each of two or more implants 1, is irradiated with direct light from the ultraviolet irradiance lamps 30 and reflection light from the reflecting mirrors 40, so that the entire surface of the protrusion 3 is irradiated with the ultraviolet rays, whereby a necessary ultraviolet irradiation treatment to the screw type implant 1 can be certainly performed. Moreover, since the surface of the stage 20 serves as the light reflecting face, so that the screw part 2 of each of the implants 1 is irradiated with the ultraviolet rays emitted from the ultraviolet ray irradiation lamps 30 through the surface of the stage 20, a necessary ultraviolet irradiation treatment to the implants 1 can be more certainly performed.

Figure 3:
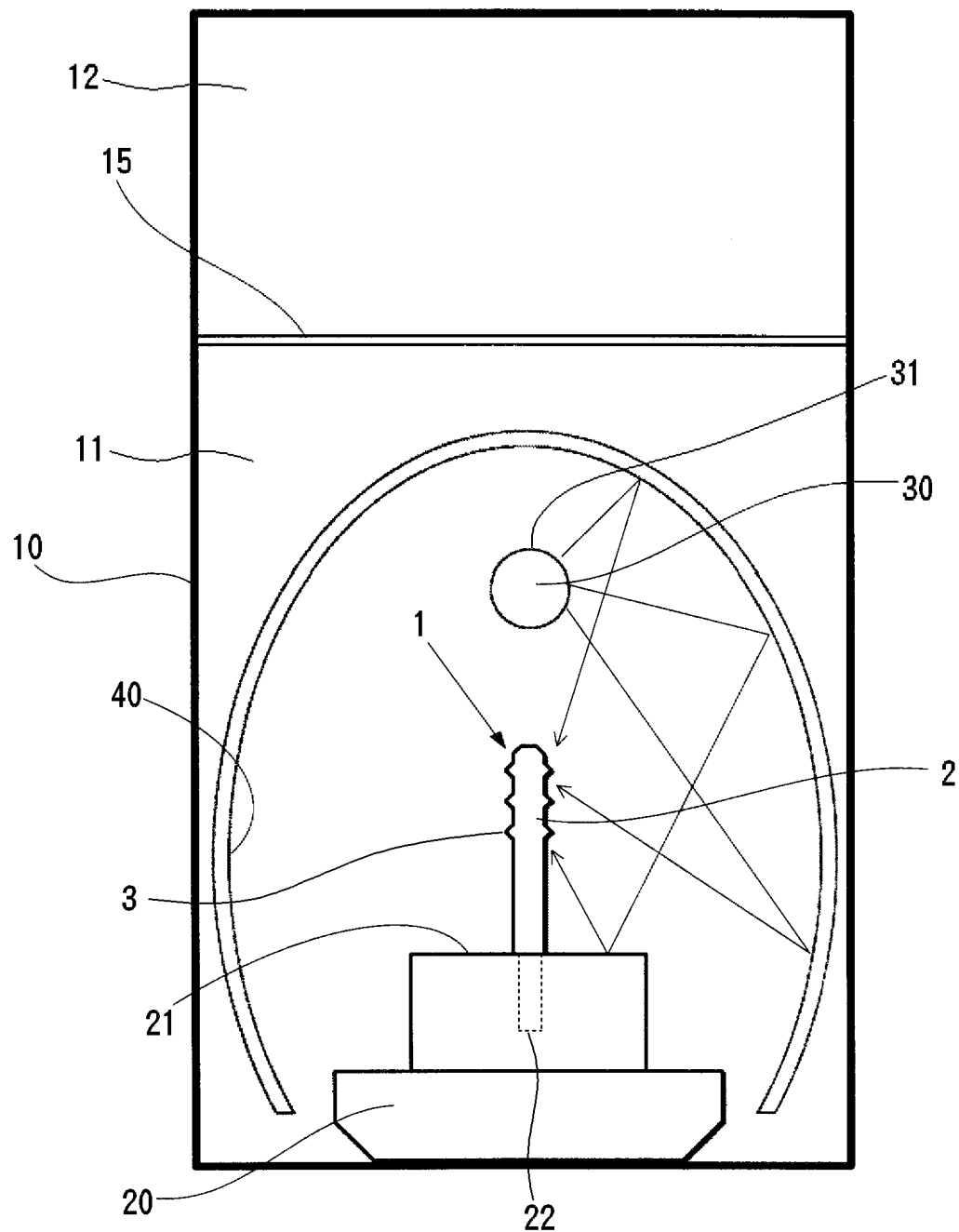
FIG. 3 It is an explanatory front view showing the structure of the inside of a casing in another example of a light irradiation device for dental implants according to the present invention.

FIG. 3 is an explanatory front view showing the structure of the inside of the casing in another example of a light irradiation device for dental implant according to the present invention. In this light irradiation device, an ultraviolet ray irradiation lamp 30, which extends in one direction where implants 1 are aligned, and which has an arc tube 31 in a shape of a straight pipe, is arranged at an upper part position of the implant group (refer to FIG. 2) which is made up of the two or more implants 1 arranged and held so as to be aligned in the one direction (a direction perpendicular to a paper face of FIG. 3) on a stage 20. A reflecting mirror 40, which reflects ultraviolet rays from the ultraviolet ray irradiation lamp 30 and which has a light reflecting face whose cross section is an approximately oval shape, is arranged so as to surround the stage 20, the implant group which is made up of the two or more implants 1 held on the stage 20, and the ultraviolet ray irradiation lamp 30. The other components of the structure are the same as those of the light irradiation device shown in FIGS. 1 and 2.

In such a light irradiation device, when the implants 1 are held in the respective holding portions 22 of the stage 20 in an orientation that the tips of screw parts 2 may face upwards, and in this condition each of the ultraviolet ray irradiation lamps 30 is turned on, the protrusions 3, which form the respective screw parts 2 of the implants 1, are directly irradiated with not only the ultraviolet rays from the ultraviolet ray irradiation lamp 30 but also those reflected by the reflecting mirror 40 and the surfaces of the stage 20, so that the entire surfaces of the protrusions 3 are irradiated with ultraviolet rays, and oxygen in atmosphere gas in a treatment room 11 is irradiated with the ultraviolet rays from the ultraviolet ray irradiation lamp 30, whereby ozone is generated in the treatment room 11, so as to be in contact with the screw parts 2 of the implants 1. Thus, while the entire surface of the protrusions 3 which form the respective screw parts 2 of the implants 1 are irradiated with the ultraviolet rays, ozone is in contact with the screw part 2, so that organic matters adhering to the screw parts 2 of the implants 1 are decomposed and removed therefrom, whereby a washing treatment of the implants 1 is attained. And after the washing treatment of the implants 1 is completed and the ultraviolet ray irradiation lamp 30 is turned off, removal of the ozone in the treatment room 11 is performed, and after that, the implants 1 are taken out of the inside of the treatment room 11. In the above embodiment, irradiation time of ultraviolet rays emitted from the ultraviolet ray irradiation lamp 30, the concentration of the ozone produced by irradiation of ultraviolet rays, and operation time of the fan 16, are the same as those of the light irradiation device shown in FIGS. 1 and 2.

In this light irradiation device, the ultraviolet ray irradiation lamp 30, which extends in the one direction where the implants 1 are aligned, and which has the arc tube 31 in a shape of a straight pipe, is arranged at the upper part position of the implant group which is made up of the two or more implants 1 arranged and held so as to be aligned in the one direction. The reflecting mirror 40, which reflects the ultraviolet rays from the ultraviolet ray irradiation lamp 30 and which has a light reflecting face whose cross section is an approximately oval shape, are arranged so as to surround the stage 20, the implant group which consists of the two or more implants 1 held on the stage 20, and the ultraviolet ray irradiation lamp 30. According to such configuration, the protrusion 3, which forms the screw part 2 of each of two or more implants 1, is irradiated with direct light from the ultraviolet irradiance lamp 30 and reflection light from the reflecting mirrors 40, so that the entire surface of the protrusion 3 is irradiated with the ultraviolet rays, whereby a necessary ultraviolet irradiation processing to the screw type implants 1 can be certainly performed. Moreover, since the surface of the stage 20 serves as the light reflecting face, so that the screw part 2 of each of the implants 1 is irradiated with the ultraviolet rays emitted from the ultraviolet ray irradiation lamp 30 through the surface of the stage 20, a necessary ultraviolet irradiation treatment to the implants 1 can be more certainly performed.

Figure 4:
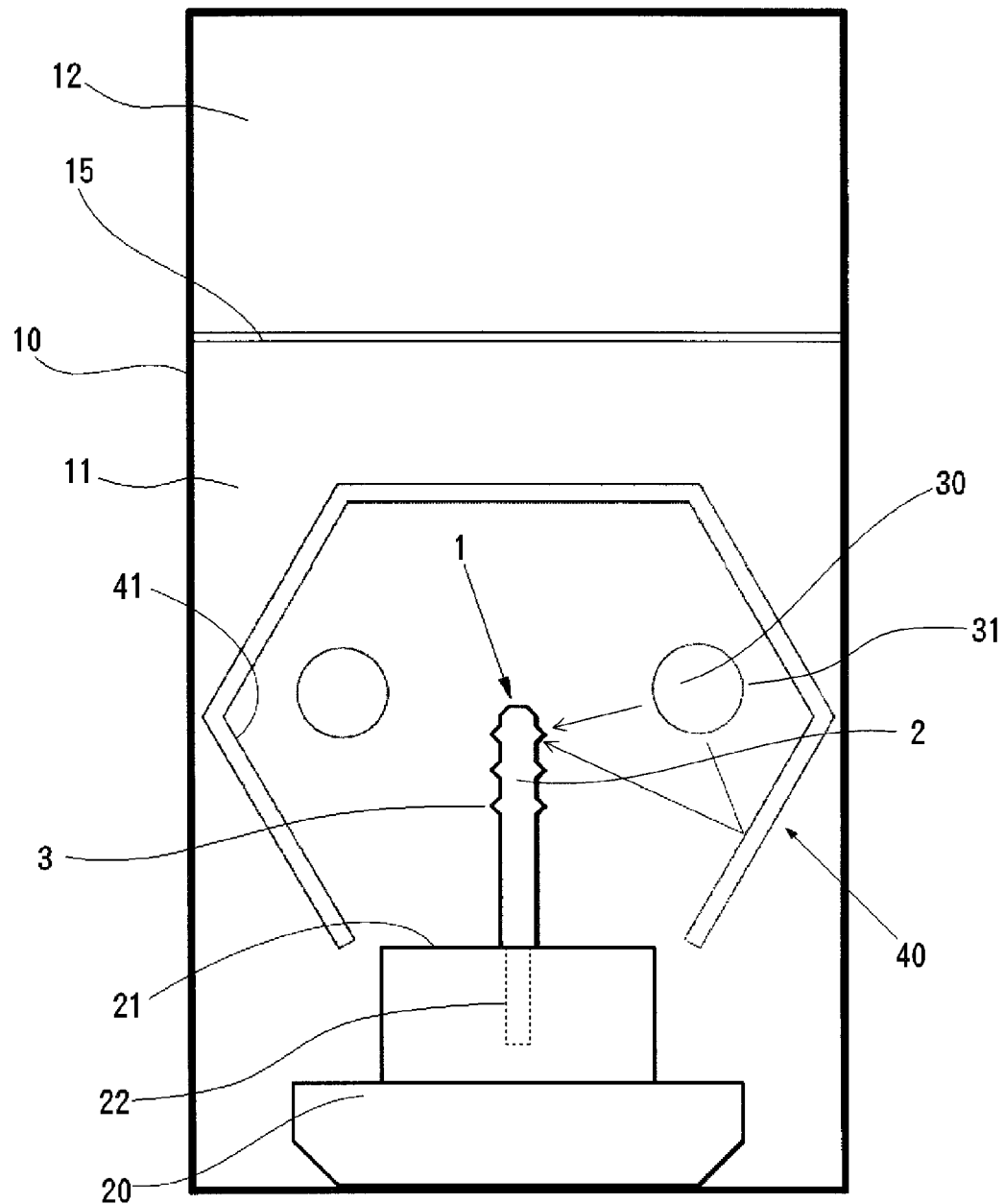
FIG. 4 It is an explanatory front view showing the structure of the inside of a casing in still another example of a light irradiation device for dental implants according to the present invention.

FIG. 4 is an explanatory front view showing the structure of the inside of a casing in still another example of a light irradiation device for dental implant according to the present invention. According to the light irradiation device, two ultraviolet irradiance lamps 30, each having the arc tube 31 in a shape of a straight pipe which extends in one direction where the implants 1 are aligned, are arranged so as to face each other, through screw parts 2 of the implants 1 and the space region of the circumference thereof, on both sides, which are parallel to the one direction in an implant group 1G (refer to FIG. 2) made up of two or more implants 1 arranged and held so as to be aligned in the one direction (a direction perpendicular to a paper sheet on which FIG. 4 is drawn) on the stage 20. A reflecting mirror 40, which is configured so that five plane mirrors 41 for reflecting ultraviolet rays from the ultraviolet ray irradiation lamps 30, respectively, are connected, one by one, to the adjoining plane mirrors 41, so as to be inclined, for example, at an angle of 120 degrees, is arranged so as to surround the stage 20, the implant group which consists of two or more implants 1 held on the stage 20, and the ultraviolet ray irradiation lamp 30. The other components of the structure are the same as those of the light irradiation device shown in FIGS. 1 and 2.

In such a light irradiation device, when the implants 1 are held in the respective holding portions 22 of the stage 20 in an orientation that the tips of the screw parts 2 may erect upwards, and in this condition, each of the ultraviolet ray irradiation lamps 30 is turned on so that the protrusions 3, which form the respective screw parts 2 of the implants 1, are directly irradiated with the ultraviolet rays from the ultraviolet ray irradiation lamps 30 and also irradiated with those reflected by the reflecting mirror 40 and the surfaces of the stage 20. As a result, the entire surfaces of the protrusions 3 are irradiated with ultraviolet rays, and oxygen in the atmosphere gas in the treatment room 11 is irradiated with the ultraviolet rays from the ultraviolet ray irradiation lamps 30, whereby ozone is generated in the treatment room 11, so as to be in contact with the screw parts 2 of the implants 1. Thus, the entire surfaces of the protrusions 3, which form the respective screw parts 2 of the implants 1, that is, both an upper face 3a and a lower face 3b of each protrusion 3 are irradiated with ultraviolet rays, and when ozone is in contact with the screw part 2, organic matters adhering to the screw parts 2 of the implants 1 are decomposed and removed therefrom, whereby a washing treatment of the implants 1 is attained. In the above embodiment, irradiation time of ultraviolet rays emitted from the ultraviolet ray irradiation lamps 30, the concentration of the ozone produced by irradiation of the ultraviolet rays, and operation time of the fan 16, are the same as those of the light irradiation device shown in FIGS. 1 and 2.

According to the light irradiation device, the two ultraviolet irradiance lamps 30 are arranged so as to face each other through the screw parts 2 of the implants 1 and the space region of the circumference thereof, on both sides, which are parallel to the one direction of the implant group 1G made up of the two or more implants 1 arranged so as to be aligned along the one direction. In addition, the reflecting mirror 40, which reflects the ultraviolet rays from the ultraviolet ray irradiation lamps 30 is arranged so as to surround the stage 20, the implant group which is made up of the two or more implants 1 held on the stage 20, and the ultraviolet ray irradiation lamps 30. According to such configuration, the protrusion 3, which forms the screw part 2 of each of two or more implants 1, is irradiated with direct light from the ultraviolet irradiance lamps 30 and with reflection light from the reflecting mirror 40, so that the entire surface of the protrusion 3 is irradiated with the ultraviolet rays, whereby a necessary ultraviolet irradiation treatment to the screw type implants 1 can be certainly performed. Moreover, since the surface of the stage 20 serves as the light reflecting face, so that the screw part 2 of each of the implants 1 is irradiated with the ultraviolet rays emitted from the ultraviolet ray irradiation lamp 30 through the surface of the stage 20, a necessary ultraviolet irradiation treatment to the implants 1 can be more certainly performed.

Although the embodiments of the light irradiation device according to the present invention are explained above, the present invention is not limited to those embodiments, and various changes can be made thereto. For example, as long as ultraviolet rays, which can produce ozone from oxygen in the air, are emitted, the ultraviolet ray irradiation lamp 30 is not limited to the low pressure mercury vapor lamp, and, for example, an excimer lamp etc. in which xenon gas etc. is enclosed, can be used. Moreover, as long as the entire surface of a protrusion 3, which forms a screw part 2 of each implant 1, is irradiated with ultraviolet rays, the form, arrangement and position of the ultraviolet ray irradiation lamp 30 and the reflecting mirror 40 can be suitably designed. For example, the shape of the arc tube 31 of the ultraviolet ray irradiation lamp 30 may not be limited to the U-shaped tube and the straight pipe shape, but one whose shape is a rectangular parallelepiped as a whole may be used. Moreover, if the surface of the protrusion 3, which forms the screw part 2 of each implant 1, is irradiated with ultraviolet rays only by direct light from the ultraviolet ray irradiation lamp 30, the reflecting mirror 40 is not needed.

REFERENCE SIGNS LIST

1 Implant
1G Implant group
2 Screw Part
3 Protrusion
3a Upper face
3b Lower face
10 Casing
11 Treatment Room
12 Ozone Removal Room
15 Dividing Wall
16 Fan
17 Ozone Removal Filter
20 Stage
21 Surface
22 Holding Portion
30 Ultraviolet ray irradiation lamp
31 Arc Tube
32 Straight Portion
33 Curve Portion
40 Reflecting Mirror
41 Plane Mirror

The invention claimed is:

1. A washing treatment device for screw type dental implants in which each of the implants has a screw part formed of a spiral protrusion, comprising:
a casing;
a treatment room provided in the casing, in which oxygen in the atmosphere gas is enclosed;
a stage; which is provided in the treatment room and which is arranged and held so that two or more dental implants are aligned in one direction; and
an ultraviolet ray irradiation lamp arranged in the treatment room,
wherein the ultraviolet ray irradiation lamp is aligned alongside the spiral protrusion, which forms the screw part of each of the dental implants held on the stage, and
wherein an entire surface of the protrusion, including an upper face and lower face of each protrusion, and the oxygen in the atmosphere gas in the treatment room are irradiated with the ultraviolet rays emitted from the ultraviolet ray irradiation lamp, so that ozone is generated in the treatment room so as to be in contact with the screw parts of the implants and organic matters adhering to the screw parts of the implants are decomposed and removed therefrom.

2. The light irradiation device for dental implants according to claim 1, wherein two ultraviolet ray irradiation lamps are arranged at both sides, which are parallel to the one direction in an implant group which is made up of the two or more dental implants held on the stage.

3. The light irradiation device for dental implants according to claim 1, wherein in the casing, a reflecting mirror which reflects the ultraviolet rays from the ultraviolet ray irradiation lamp is arranged, and the entire surface of the protrusion which forms the screw part of each of the two or more dental implants is irradiated with the ultraviolet rays in form of direct light from the ultraviolet ray irradiation lamp and reflection light from the reflecting mirror.

4. The light irradiation device for dental implants according to claim 1, wherein the surface of the stage serves as a light reflecting face.

5. The light irradiation device for dental implants according to claim 2, wherein in the casing, a reflecting mirror which reflects the ultraviolet rays from the ultraviolet ray irradiation lamp is arranged, and the entire surface of the protrusion which forms the screw part of each of the two or more dental implants is irradiated with the ultraviolet rays in form of direct light from the ultraviolet ray irradiation lamp and reflection light from the reflecting mirror.

6. The light irradiation device for dental implants according to claim 1, wherein an ozone removal room, which removes ozone produced in the treatment room, is formed above the treatment room.

7. The light irradiation device for dental implants according to claim 1, wherein a fan is provided in the casing.

8. The light irradiation device for dental implants according to claim 1, wherein the stage has holding portions, each of which consists of a concave portion whose inner diameter matches an outer diameter of the other end part of the implant.

9. The light irradiation device for dental implants according to claim 8, wherein the holding portions are formed on the stage so as to be aligned along the one direction.

* * * * *